US012584150B2

(12) United States Patent
Manning et al.

(10) Patent No.: US 12,584,150 B2
(45) Date of Patent: Mar. 24, 2026

(54) ENDOGENOUS LIPASE FOR METAL REDUCTION IN DISTILLERS CORN OIL

(71) Applicant: POET Research, Inc., Sioux Falls, CO (US)

(72) Inventors: Andrew J. Manning, Sioux Falls, SD (US); Alex T. McCurdy, Sioux Falls, SD (US); Steven T. Bly, Sioux Falls, SD (US)

(73) Assignee: POET Research, Inc., Sioux Falls, SD (US)

( * ) Notice: Subject to any disclaimer, the term of this patent is extended or adjusted under 35 U.S.C. 154(b) by 0 days.

(21) Appl. No.: 18/634,304

(22) Filed: Apr. 12, 2024

(65) Prior Publication Data

US 2024/0392327 A1     Nov. 28, 2024

Related U.S. Application Data

(62) Division of application No. 17/395,282, filed on Aug. 5, 2021, now Pat. No. 11,987,832.

(60) Provisional application No. 63/062,135, filed on Aug. 6, 2020.

(51) Int. Cl.
| | |
|---|---|
| *C12P 7/64* | (2022.01) |
| *C11B 3/00* | (2006.01) |
| *C12N 9/20* | (2006.01) |
| *C12P 7/06* | (2006.01) |
| *C12P 7/14* | (2006.01) |

(52) U.S. Cl.
CPC ...................................... *C12P 7/14* (2013.01)

(58) Field of Classification Search
CPC .... C12P 7/64; C12P 7/06; C11B 13/00; C11B 3/00; C12N 9/20; C12N 9/02; C12N 9/007; C12N 9/04; A23D 9/04
See application file for complete search history.

(56) References Cited

U.S. PATENT DOCUMENTS

| | | | |
|---|---|---|---|
| 1,247,782 | A | 11/1917 | Ayres |
| 1,737,402 | A | 11/1929 | Ayres |
| 2,510,379 | A | 6/1950 | Christenson |
| 2,510,402 | A | 6/1950 | Johnston |
| 2,762,780 | A | 9/1956 | Kulakow |
| 2,881,195 | A | 4/1959 | Hayes |
| 3,354,188 | A | 11/1967 | Bock |
| 4,049,686 | A | 9/1977 | Ringers et al. |
| 4,609,500 | A | 9/1986 | Strecker |
| 4,698,185 | A | 10/1987 | Dijkstra et al. |
| 4,713,155 | A | 12/1987 | Arutjuanian et al. |
| 5,208,054 | A | 5/1993 | Torrii et al. |
| 5,239,096 | A | 8/1993 | Rohdenburg et al. |
| 5,512,691 | A | 4/1996 | Barnicki et al. |
| 5,516,924 | A | 5/1996 | van de Sande et al. |
| 6,015,915 | A | 1/2000 | Jamil et al. |
| 6,033,706 | A | 3/2000 | Silkeberg et al. |

| | | | |
|---|---|---|---|
| 6,074,863 | A | 6/2000 | Svendsen et al. |
| 6,103,918 | A | 8/2000 | Dahlen |
| 6,407,271 | B1 | 6/2002 | Deffense |
| 6,426,423 | B1 | 7/2002 | Copeland et al. |
| 6,514,332 | B2 | 2/2003 | Varnadoe et al. |
| 6,743,930 | B2 | 6/2004 | Li |
| 6,764,542 | B1 | 7/2004 | Lackey et al. |
| 6,776,832 | B2 | 8/2004 | Spence et al. |
| 6,844,458 | B2 | 1/2005 | Copeland et al. |
| 6,924,381 | B2 | 8/2005 | Dawson |
| 7,122,216 | B2 | 10/2006 | Copeland et al. |
| 7,582,458 | B2 | 9/2009 | Grichko |
| 7,601,858 | B2 | 10/2009 | Cantrell et al. |
| 7,696,369 | B2 | 4/2010 | Kellens et al. |
| 7,713,727 | B2 | 5/2010 | Dayton et al. |
| 7,842,484 | B2 | 11/2010 | Lewis |
| 7,879,917 | B2 | 2/2011 | Cheng et al. |
| 7,893,115 | B2 | 2/2011 | Cheng et al. |
| 7,919,291 | B2 | 4/2011 | Lewis et al. |
| 8,008,516 | B2 | 8/2011 | Cantrell et al. |
| 8,076,123 | B2 | 12/2011 | Chou |
| 8,114,926 | B2 | 2/2012 | Dupuis et al. |
| 8,163,059 | B2 | 4/2012 | Tran et al. |
| 8,232,418 | B1 | 7/2012 | Bilbie et al. |

(Continued)

FOREIGN PATENT DOCUMENTS

| | | |
|---|---|---|
| BR | PI0704791 | 7/2009 |
| EP | 2656834 | 10/2013 |

(Continued)

OTHER PUBLICATIONS

Abdulkadir et al. (2017) "Production and refining of corn oil from hominy feed a by-product of dehulling operation" ARPN Journal of Engineering an Applied Sciences 6(4):7 pages.
Back-End Value Enhanced through Patented Technology and Strategic Partnerships retrieved from www.valicor.com (5 pages).
Bailey (2010) "Novel uses of vegetable oil in asphalt mixtures" Ph.D. Thesis, University of East London, UK, Sep. 2010) 366 pgs.
Bailey (2012) "The use of vegetable oil as a rejuvenator for asphalt mixtures" 5th Eurasphalt and Eurobitume Congress, Istanbul, (Jun. 13-15, 2012) 10 pgs.

(Continued)

*Primary Examiner* — Maryam Monshipouri
(74) *Attorney, Agent, or Firm* — FisherBroyles, LLP; Cara L. Crowley-Weber; Cary Reeves

(57) ABSTRACT

Provided herein are compositions, methods, systems associated with propagation and fermentation, and co-products of biochemical production processes, for example, a DCO co-product resulting from converting oil containing grains into bio chemicals via fermentation in the presence of endogenous esterase. The DCO resulting from the processes exhibits lower metal ion content relative to a DCO obtained in the absence of endogenous fermentation with an esterase such as a lipase. The DCO is useful as a feedstock for the production of renewable diesel.

18 Claims, No Drawings

Specification includes a Sequence Listing.

(56)  References Cited

U.S. PATENT DOCUMENTS

| | | | |
|---|---|---|---|
| 8,435,766 | B2 | 5/2013 | Kellens et al. |
| 8,476,047 | B2 | 7/2013 | Burlew et al. |
| 8,608,845 | B2 | 12/2013 | Naidoo et al. |
| 8,637,290 | B2 | 1/2014 | O'Donoghue et al. |
| 8,702,819 | B2 | 4/2014 | Bootsma |
| 8,759,044 | B2 | 6/2014 | Dicosimo et al. |
| 8,765,425 | B2 | 7/2014 | Dicosimo et al. |
| 8,765,985 | B2 | 7/2014 | Hora et al. |
| 8,808,445 | B2 | 8/2014 | Coe |
| 8,901,330 | B2 | 12/2014 | Doyle et al. |
| 8,962,059 | B1 | 2/2015 | Froderman et al. |
| 9,045,712 | B2 | 6/2015 | Dayton et al. |
| 9,061,987 | B2 | 6/2015 | Bootsma |
| 9,109,179 | B2 | 8/2015 | Cowin et al. |
| 9,139,803 | B2 | 9/2015 | Redford |
| 9,144,758 | B2 | 9/2015 | Wang et al. |
| 9,228,211 | B2 | 1/2016 | Soe et al. |
| 9,255,239 | B1 | 2/2016 | Wiese |
| 9,290,728 | B2 | 3/2016 | Bootsma |
| 9,340,749 | B1 | 5/2016 | Kozyuk et al. |
| 9,388,100 | B2 | 7/2016 | Redford |
| 9,416,274 | B2 | 8/2016 | Frank |
| 9,453,180 | B2 | 9/2016 | Kozyuk et al. |
| 9,481,794 | B2 | 11/2016 | Cox et al. |
| 9,481,853 | B2 | 11/2016 | Gordon et al. |
| 9,534,182 | B1 | 1/2017 | Ballard |
| 9,534,184 | B2 | 1/2017 | Thompson et al. |
| 9,556,399 | B2 | 1/2017 | Kozyuk et al. |
| 9,617,425 | B1 | 4/2017 | Moriyasu et al. |
| 9,695,449 | B2 | 7/2017 | Bootsma |
| 9,765,280 | B2 | 9/2017 | Kurth et al. |
| 9,783,458 | B2 | 10/2017 | Martin |
| 9,896,643 | B2 | 2/2018 | Redford |
| 9,961,916 | B2 | 5/2018 | Arhancet et al. |
| 10,087,397 | B2 | 10/2018 | Phillips et al. |
| 10,113,187 | B2 | 10/2018 | Bushong et al. |
| 10,167,390 | B2 | 1/2019 | Cox |
| 10,323,148 | B1 | 6/2019 | Brewster et al. |
| 10,526,564 | B2 | 1/2020 | Phillips et al. |
| 10,526,623 | B2 | 1/2020 | Bootsma |
| 10,584,304 | B2 | 3/2020 | Schnell et al. |
| 10,604,776 | B2 * | 3/2020 | McCurdy ................. C12P 7/06 |
| 10,711,221 | B2 | 7/2020 | Lamprecht et al. |
| 10,781,464 | B2 | 9/2020 | Yoshida et al. |
| 10,815,430 | B2 | 10/2020 | Gutierrez et al. |
| 10,815,506 | B2 | 10/2020 | Rancke-Madsen et al. |
| 10,851,327 | B2 | 12/2020 | Urban et al. |
| 10,899,928 | B2 | 1/2021 | McCurdy et al. |
| 11,008,531 | B2 | 5/2021 | Lamprecht et al. |
| 11,104,922 | B2 | 8/2021 | McCurdy et al. |
| 2004/0063184 | A1 | 4/2004 | Grichko |
| 2006/0041152 | A1 | 2/2006 | Cantrell et al. |
| 2006/0089429 | A1 | 4/2006 | Buras et al. |
| 2006/0215483 | A1 | 9/2006 | Helf |
| 2008/0006889 | A1 | 1/2008 | Diamond et al. |
| 2008/0146851 | A1 | 6/2008 | Schonemann et al. |
| 2008/0176298 | A1 | 7/2008 | Randhava et al. |
| 2008/0314294 | A1 | 12/2008 | White et al. |
| 2009/0137705 | A1 | 5/2009 | Faucon Dumont et al. |
| 2009/0306419 | A1 | 12/2009 | Myong et al. |
| 2010/0034586 | A1 | 2/2010 | Bailey et al. |
| 2010/0058649 | A1 | 3/2010 | Bootsma |
| 2010/0125356 | A1 | 5/2010 | Shkolnik |
| 2010/0191360 | A1 | 7/2010 | Napadensky |
| 2011/0086149 | A1 | 4/2011 | Bootsma |
| 2011/0093965 | A1 | 4/2011 | O'Donoghue |
| 2012/0060722 | A1 | 3/2012 | Montpeyrous et al. |
| 2012/0245370 | A1 | 9/2012 | Sheppard et al. |
| 2013/0157324 | A1 * | 6/2013 | Dicosimo ................. C12P 7/62 |
| | | | 435/254.2 |
| 2014/0230693 | A1 | 8/2014 | Gonzalez et al. |
| 2014/0371895 | A1 | 12/2014 | Sadusk |
| 2015/0230488 | A1 | 8/2015 | de Man et al. |
| 2015/0291923 | A1 | 10/2015 | Bootsma |
| 2016/0145650 | A1 | 5/2016 | Lewis et al. |
| 2016/0185044 | A1 | 6/2016 | Leonard |
| 2016/0250810 | A1 | 9/2016 | Lynch |
| 2017/0022364 | A1 | 1/2017 | Cox |
| 2017/0066995 | A1 | 3/2017 | Borst et al. |
| 2017/0107449 | A1 | 4/2017 | Hruschka et al. |
| 2017/0107452 | A1 | 4/2017 | Sarai et al. |
| 2017/0145642 | A1 | 5/2017 | Swanson |
| 2017/0283838 | A1 | 10/2017 | Bootsma |
| 2017/0304894 | A1 | 10/2017 | Buller |
| 2018/0273988 | A1 | 9/2018 | Lewis et al. |
| 2018/0340067 | A1 | 11/2018 | McCurdy et al. |
| 2018/0340068 | A1 | 11/2018 | McCurdy et al. |
| 2018/0340197 | A1 * | 11/2018 | McCurdy ................. C11B 13/00 |
| 2019/0249109 | A1 | 8/2019 | Lamprecht et al. |
| 2019/0376002 | A1 | 12/2019 | Urban et al. |
| 2020/0063168 | A1 | 2/2020 | Bootsma |
| 2020/0131403 | A1 | 4/2020 | McCurdy |
| 2020/0165642 | A1 | 5/2020 | McCurdy et al. |
| 2020/0299610 | A1 | 9/2020 | Marques de Lima |
| 2021/0032564 | A1 | 2/2021 | Urban et al. |
| 2021/0332244 | A1 | 10/2021 | McCurdy et al. |

FOREIGN PATENT DOCUMENTS

| | | |
|---|---|---|
| EP | 2689006 | 1/2014 |
| EP | 2264157 | 5/2014 |
| GB | 481580 | 3/1938 |
| GB | 766394 | 1/1957 |
| GB | 1065720 | 4/1967 |
| GB | 1562380 | 3/1980 |
| JP | 005154467 | 6/2005 |
| JP | 4257188 | 4/2009 |
| WO | WO 8802775 | 4/1988 |
| WO | WO 9323508 | 11/1993 |
| WO | WO 9421762 | 9/1994 |
| WO | WO 9801518 | 1/1998 |
| WO | WO 2004007654 | 1/2004 |
| WO | WO 2004081193 | 9/2004 |
| WO | WO 2008061120 | 5/2008 |
| WO | WO 2009120419 | 10/2009 |
| WO | WO 2010053244 | 5/2010 |
| WO | WO 2010077141 | 7/2010 |
| WO | WO 2012109221 | 8/2012 |
| WO | WO 2012129548 | 9/2012 |
| WO | WO 2014037008 | 3/2014 |
| WO | WO 2014158011 | 10/2014 |
| WO | WO 2015168020 | 11/2015 |
| WO | WO 2015181308 | 12/2015 |
| WO | WO 2016003465 | 1/2016 |
| WO | WO 2016178676 | 11/2016 |
| WO | WO 2018024654 | 2/2018 |
| WO | WO 2018031540 | 2/2018 |
| WO | WO 2018217198 | 11/2018 |
| WO | WO 2018218033 | 11/2018 |
| WO | WO 2019069992 | 4/2019 |

OTHER PUBLICATIONS

Bailey (2012) "The use of vegetable oil in asphalt mixtures, in the laboratory and field" 5th Eurasphalt and Eurobitume Congress, Istanbul, (Jun. 13-15, 2012) 12 pgs.

Barros et al. (2010) "Seed lipases: sources, application and properties—a review" Brazilian J of Chem Engineering 27(1):15-29.

Bennert et al. (2016) "Fatigue performance of Re-refined Engine Oil Bottoms (REOB) modified asphalt—a laboratory study" 95th Annual Transportation Research Board Meeting.

Brothers et al. (2018) "Free fatty-acid generation and lipid oxidation during dry-grind corn ethanol fermentation" J American Oil Chem Soc 95(12):1521-1533.

Cesarini et al. (2015) "Moving towards a competitive fully enzymatic biodiesel process" Sustainability 7:7884-7903.

Corn Oil, Retrieved from https://com.org/resources/?fwp_resource_type=pdf&fwp_search=corn%20oil, 2006 24 pages.

D'Amore et al. (1990) "A study of ethanol tolerance in yeast" Critical Reviews in Biotechnology 9:4.

D'Amore et al. (1987) "Ethanol tolerance of yeast" Enzyme and Microbial Technology 9:6-17.

(56)            References Cited

OTHER PUBLICATIONS

Defoamer Retrieved from https://en.wikipedia.org/wiki/defoamer on May 30, 2019, 5 pages.

European Search Report for Application No. 18806452.1, PCT/US201803441, dated Feb. 1, 2021, 9 pages.

Friedrich et al. (1984) "Properties and processing of corn oils obtained by extraction with supercritical carbon dioxide" JAOCS 61:12-15.

Gibbons et al. (2009) "Integrated biorefineries with engineered microbes and high-value co-products for profitable 2 biofuels production" In Vitro Cellular & Development Biology Plant 45(3):218-228, XP055270849, US ISSN: 1054-5476, DOI: 10.1007/s11627-009-9202-1, 10 pages.

Golalipour (2013) "Investigation of the Effect of Oil Modification on Critical Characteristics of Asphalt Binders" Ph.D. Dissertation, U. of Wisconsin—Madison, [Online], Retrieved from the Internet: <URL: http://www.asphaltinstitute.org/wp-content/uploads/Thickness Mix/PhDDissertationDocument-Final-AG2.pdf>, 204 pages.

Hughes et al. (2011) "Production of Candida antarctica lipase B gene open reading frame using automated PCR gene assembly protocol on robotic work cell and expression in an ethanologenic yeast for use as resin-bound biocatalyst in biodiesel production" Journal of the Association for Lab. Automation 16(1):17-37.

International Search Report and Written Opinion from Application Serial No. PCT/US2017/034262, mailed Mar. 23, 2018, 7 pages.

International Search Report and Written Opinion for Application Serial No. PCT/US2018/034410, mailed Jan. 17, 2019, 6 pages.

International Search Report for Application No. PCT/US2019/036578, mailed May 14, 2019, 6 pages.

International Search Report for Application No. PCT/US2019/036578, mailed Oct. 11, 2019, 5 pages.

Japir et al. "Separation of free fatty acids from high free fatty acid crude palm oil using short path distillation" 2016 UKM Fest Postgraduation Collegium AIP Conf Proc. 1784 03001-1-030001-8 9 pages.

Layfield et al. (2015) "What brewers should know about viability, vitality, and overall brewing fitness: a mini-review" Master Brew Assoc Am. 52:3-12.

LCI Corporation "Short path evaporation" retrieved from https://lcicorp.com/short_path_evaporators/short_path_evaporator 2 pages.

Meng et al. (2011) "Two-step synthesis of fatty acid ethyl ester from soybean oil catalyzed by Yarrowia lipolytica lipase" Biotechnology for Biofuels 4(6):9 pages.

Micro-fine silica treated with an organic silicone compound, DUMACIL® 100 FGK, Elementis Specialties Apr. 2017 1 page.

Mogawer et al. (2013) "Evaluating the effect of rejuvenators on the degree of blending and performance of high RAP, RAS, and RAP/RAS mixtures" Road Materials and Pavement Design 14(2):29 pages.

Moghaddam (2016) "The use of rejuvenating agents in production of recycled hot mix asphalt: a systematic review" Construction and Building Materials 114:805-816.

Moreau et al. (2010) "Changes in lipid composition during dry grind ethanol processing of corn" Journal of the American Oil Chemist's Society 88:9 pages.

Oliveira et al. (1991) "Production and extractive biocatalysis of ethanol using microencapsulated yeast cells and lipase system" J of Chem Tech & Biotech 52(2):1231-1238.

Oliveira et al. (1998) "In situ recovery of ethanol by extraction and enzymatic esterification" Med Fac Fandouw 63:1231-1238.

Saini et al. (2018) "Carotenoid extraction methods: a review of recent developments" Food Chemistry 240:90-103.

Seidel et al. (2014) "Rheological characterization of asphalt binders modified with soybean fatty acids" Construction and Building Materials 53:324-332.

Skaliotis (2011) "Short path to premium quality oils" Food Marketing and Technology pp. 23-26.

Standard Test Method for Foaming Properties of Surface-Active Agents (2001) Designation D 1173-53 Reapproved 2 pages.

Tesfaw et al. (2014) "Current trends in bioethanol production by *Saccharomyces cerevisiae*: substrate, inhibitor reduction, growth variables, coculture and immobilization" International Scholarly Research Notices pp. 1-11.

Van Den Berg et al. (2013) "Simultaneous clostridial fermentation, lipase-catalyzed esterification, and ester extraction to enrich diesel with butyl butyrate" Biotechnology and Bioenaineerina 11(1): 6 pages.

Winkler et al. (2007) "Phytosterol and tocopherol components in extracts of corn distiller's dried grain" J Agric Food Chem 55(16):6482-6486.

Winkler-Moser (2011) "Composition and oxidative stability of crude oil extracts of corn germ and distillers Grains" Industrial Crops and Products 33:572-578.

Winkler-Moser et al. (2009) "Antioxidant activity of phytochemicals from distillers dried grain oil" Journal of the American Oil Chemist's Society 86:1073-1082.

Yusoff et al. (2014) "Comparison of fatty acid methyl and ethyl esters as biodiesel base stock: a review on processing and production requirements" J Am Oil Chem Soc 91:525-531.

Zaumanis (2013) "Use of rejuvenators for production" VIII International Baltic Road Conference, 10 pages.

Zaumanis et al. (2014) "Influence of six rejuvenators on the performance properties of Reclaimed Asphalt Pavement (RAP) binder and 100% recycled asphalt mixtures" Construction and Building Materials 71: 14 pages.

* cited by examiner

ENDOGENOUS LIPASE FOR METAL REDUCTION IN DISTILLERS CORN OIL

RELATED APPLICATIONS

This application is a divisional of U.S. application Ser. No. 17/395,282, titled "Endogenous Lipase for Metal Reduction in Distillers Corn Oil" filed Aug. 5, 2021, and also claims the benefit of U.S. Provisional application No. 63/062,135 titled "Endogenous Lipase for Metal Reduction in Distillers Corn Oil" filed Aug. 6, 2020. Each of the priority applications are incorporated herein by reference.

TECHNICAL FIELD

Provided herein are methods, compositions, and systems for propagation and fermentation, particularly in large scale operations for production of ethanol dried distillers grain, and distillers corn oil.

SEQUENCE LISTING

A copy of the sequence listing is submitted concurrently with the specification electronically via Patent Center. The contents of the electronic sequence listing (PT-150-US03_Sequence_Listing_2024-8-12. xml; Size: 45,056 bytes; and Date of Creation: Aug. 12, 2024) are incorporated herein by reference.

BACKGROUND

Ethanol can be produced from grain-based feedstocks (e.g. corn, sorghum/milo, barley, wheat, soybeans, etc.), from sugar (e.g. sugar cane, sugar beets, etc.), or from cellulosic biomass (e.g. lignocellulosic feedstocks, such as switchgrass, corn cobs and stover, wood or other plant material).

Conventional ethanol plants utilize corn as a feedstock and ethanol is produced from the starch within the corn. Corn kernels are cleaned and milled to prepare starch-containing material for processing. The starch-containing material is slurried with water and liquefied to promote saccharification and fermentation. Saccharification is the conversion of starch into sugar (e.g. glucose) and fermentation is the conversion of sugar into ethanol by an ethanologen (e.g. yeast). Fermentation yields a liquid component (ethanol, water, and soluble components) and a solids component (unfermented particulate matter). The fermentation product is distilled and dehydrated into ethanol. The residual matter or whole stillage contains water, soluble components, oil, syrup, and unfermented solids. The solids can be dried into dried distillers' grains (DDGs) and sold as animal feed product. Similarly, the other products can also be recovered and utilized such as oil for use as renewable diesel.

SUMMARY

Corn oil produced as a by-product of commercial ethanol fermentation, distillers corn oil (DCO), may contain enhanced levels of metal, which are detrimental for producing renewable diesel. Lipase treatment during fermentation greatly reduces the metal content, also referred to herein as "metal ion content", of DCO.

Provided herein are compositions, methods, systems associated with propagation and fermentation, and co-products of biochemical production processes, for example, a DCO co-product resulting from converting oil containing grains into bio chemicals via fermentation. The DCO is useful as a feedstock for the production of renewable diesel.

Provided herein are compositions comprising a primary feedstock, yeast, an esterase-producing organism, and water. The primary feedstock comprises the sugar source for propagation and fermentation by the microorganisms.

Provided herein are methods of reducing metal content in DCO produced as a co-product of ethanol production by utilizing an esterase-producing microorganism in propagation, fermentation, and/or in a side-tank propagation. The methods comprise (a) combining a feedstock, an ethanologen (e.g. yeast), an esterase-producing microorganism, and water in a propagator, side-tank, and/or fermenter; and (b) fermenting the feedstock. In some aspects, the esterase-producing microorganism is a yeast or bacteria. In some aspects, the ethanologen is also an esterase-producing organism (e.g. the ethanologen is able to produce both ethanol and esterase).

In some embodiments provided herein, the esterase-producing microorganism is genetically modified to produce a carboxylic esterase (e.g. lipase).

In some embodiments provided herein, the esterase-producing microorganism is genetically modified to produce a CALB lipase.

Provided herein are methods of producing DCO. The methods comprise: (a) inoculating a feedstock: (i) with a combination of a first microorganism for fermentation of the feedstock, i.e. an ethanologen, and a second microorganism for producing lipase; (ii) with a yeast for fermentation, i.e. an ethanologen or fermentation yeast, of the feedstock, wherein the yeast is genetically modified to produce lipase; or (iii) with a yeast strain for fermentation of the feedstock, i.e. an ethanologen, wherein the feedstock contains starch from a genetically modified plant engineered to produce lipase; and (b) fermenting the feedstock to produce ethanol and DCO.

In some aspects, step (a)(i) includes inoculating a feedstock in a propagation tank or a fermentation tank with the ethanologen and the second microorganism.

In some aspects, step (a)(i) includes inoculating a feedstock in a first propagation tank with the ethanologen and inoculating a feedstock in a second propagation tank (side tank propagation) with the second microorganism. In some aspects, step (b) further comprises fermenting contents obtained from the first propagation tank with contents obtained from the second propagation tank in the presence of feedstock for ethanol production.

In some aspects, step (a)(i) includes inoculating a feedstock in a fermentation tank with the ethanologen and inoculating a feedstock in a propagation tank (side tank propagation) with the second microorganism, and wherein step (b) further comprises adding the contents obtained from the propagation tank to the fermentation tank and fermenting feedstock for ethanol production.

In some aspects, step (a)(iii) includes a feedstock containing starch from a genetically modified plant engineered to produce lipase. The genetically modified plant can be, for example, corn, soybean, cottonseed, sunflower seed, canola, rapeseed, or peanut. Corn is used throughout the disclosure as an exemplary plant modified to produce lipase, such that the feedstock obtained from the corn plant contains sufficient levels of lipase useful in the processes and compositions provided herein. However, it is understood that any plant useful as a feedstock and genetically modified to produce lipase will be useful in the processes and compositions provided herein.

Propagation and/or fermentation with endogenously produced esterases, e.g. lipases, DCO with certain desirable properties. In some aspects, the DCO exhibits decreased levels of cationic metals ($Na^+$, $K^+$, $Mg^{2+}$, $Ca^{2+}$, etc.) relative to the levels of cationic metals present in DCO produced in the absence of a lipase-producing microorganism, yeast, or plant. In some aspects, the DCO exhibits decreased soap content and higher oil yield relative to the soap content in DCO produced in the absence of a lipase-producing microorganism, yeast, or plant. In some aspects, the DCO exhibits decreased viscosity relative to the viscosity of a DCO produced in the absence of a lipase-producing microorganism, yeast, or plant. In some aspects, the DCO comprises increased FAEE/decreased FFA relative to the FAEE/FFA content of a DCO produced in the absence of a lipase-producing microorganism, yeast, or plant. In some aspects, FAEE is increased anywhere from 1 to 5× and FFA are decreased anywhere from 1 to 5×, relative to the FAEE and FFA content of a DCO produced in the absence of a lipase-producing microorganism, yeast, or plant. In some aspects, FAEE is increased and FFA are decreased in a 1:1 ratio, relative to the FAEE and FFA content of a DCO produced in the absence of a lipase-producing microorganism, yeast, or plant. The change in FAEE/FFA content correlates with the decrease in metal ions content, but not necessarily in a linear or 1:1 fashion.

The lipase endogenous to the plant used as feedstock, i.e. a crop plant genetically modified to produce lipase or another esterase useful herein, e.g. corn used as feedstock, or the lipase produced by the microorganism in the propagation or fermentation, is present in the fermentation broth in an amount equivalent to about 0.01 to about 1.00 LU/g dry solids (DS); about 0.0001% to about 0.0300% w/w DS; about 0.02% to about 0.5% w/w corn oil; or about 1 L to about 100 L in a 550,000 gal fermentation vat. In some aspects, the lipase produced is present in an amount sufficient to reduce metal ion content in DCO to less than about 10 ppm. In some aspects, the lipase produced is present in the fermentation in an amount sufficient to reduce FFA content in DCO to less than about 15% relative to a fermentation in the absence of a lipase-producing microorganism, yeast, or plant. In some aspects, the lipase produced is present in the fermentation in an amount sufficient to reduce metal ion content in DCO by at least about 10% to about 100%, e.g. at least about 10% to about 90%, at least about 20% to about 90%, at least about 30% to about 90%, at least about 40% to about 90%, at least about 50% to about 90%, at least about 60%, at least about 70%, at least about 80%, at least about 90%, or about 100%, relative to a fermentation in the absence of a lipase-producing microorganism, yeast, or plant.

In some embodiments, as provided in 1(a)(i), the ethanologen is *S. cerevisiae* and the second microorganism is a genetically modified yeast engineered to produce lipase. The lipase produced by the second yeast is present in the fermentation in an amount sufficient to reduce metal ion content in DCO by at least about 10% to at about 100% relative to a fermentation in the absence of a lipase-producing microorganism, yeast, or plant.

In some embodiments, as provided in 1(a)(i), the ethanologen is *S. cerevisiae* and the second microorganism is a bacteria engineered to produce lipase. The lipase produced by the bacteria is present in the fermentation in an amount sufficient to reduce metal ion content in DCO by at least about 10% to about 100% relative to a fermentation in the absence of a lipase-producing microorganism, yeast, or plant.

In some embodiments, as provided in 1(a)(ii), the yeast is *S. cerevisiae*. In some aspects, the lipase produced by the yeast is present in the fermentation in an amount equivalent to about 0.03 to about 0.70 LU/g dry solids (DS). In some aspects, the lipase produced by the yeast is present in the fermentation in an amount sufficient to reduce metal ion content in DCO by at least about 10% to about 100% relative to a fermentation in the absence of a lipase-producing microorganism, yeast, or plant.

Provided herein are compositions for commercial production of ethanol. In some embodiments, the composition comprises two microorganisms: an ethanologen which is a yeast strain and a second microorganism which is a yeast strain or bacteria genetically modified to produce lipase under conditions for ethanol production. In some aspects, the ethanologen is *S. cerevisiae*. In some aspects, the second microorganism is a bacteria. In some aspects, the second microorganism is a yeast strain. In some aspects, the second microorganism is *S. cerevisiae*. In some embodiments, composition comprises one microorganism: an ethanologen, such as yeast strain for fermentation of a feedstock but which is genetically modified to produce lipase under conditions for ethanol production. In some embodiments, the composition comprises an ethanologen, such as a yeast strain for fermentation of a feedstock under conditions for ethanol production, and ground corn obtained from a genetically modified plant which produces an esterase such as lipase.

The conditions for ethanol production are selected from the group consisting of:
(i) anaerobic fermentation;
(ii) fermentation solids content of at least about 20%;
(iii) a pH of about 4.0 to about 5.0; and
(iv) a temperature of about 25° C. to about 37° C., or about 30° C. to about 34° C.

Provided herein are fermenters comprising water, feedstock, an ethanologen, and a second microorganism which is a yeast strain or bacteria genetically modified to produce lipase under conditions for ethanol production.

Also provided herein are fermenters comprising water, feedstock, and an ethanologen such as a yeast strain which is genetically modified to produce lipase under conditions for ethanol production.

Also provided herein are fermenters comprising water, an ethanologen, such as a yeast strain for fermentation of a feedstock under conditions for ethanol production, and ground feedstock obtained from a genetically modified plant which produces an esterase such as lipase. The genetically modified plant can be corn, soybean, cottonseed, sunflower seed, canola, rapeseed, or peanut.

Provided herein are methods of producing DCO as a by-product of fermentation associated with ethanol production. In some aspects, the method comprises: (a) inoculating a feedstock with a combination of two yeast strains, wherein the first yeast strain is an ethanologen and the second yeast strain produces lipase; and (b) fermenting the feedstock to produce ethanol and DCO, wherein the metal ions content in the DCO is decreased by at least about 10% relative to a DCO obtained as the by-product of fermentation in the absence of a lipase producing yeast. In some aspects, the ethanol titer is unchanged relative to the same fermentation performed in the absence of the lipase expressing yeast strain.

Provided herein are methods of producing DCO. The methods comprise providing a first composition comprising water and ground corn; inoculating the first composition with: (i) a combination of a first yeast for fermentation of the ground corn, i.e. an ethanologen or fermentation yeast, and a second yeast engineered to produce lipase; or (ii) an ethanologen genetically modified to produce lipase; under conditions to form a second composition comprising oil, wherein the lipase produced is sufficient to reduce metal ion content in DCO; and isolating DCO from the second composition, wherein the metal ions content in the DCO is decreased relative to a DCO produced in the absence of a lipase producing yeast.

Provided herein are methods of producing DCO. The methods comprise providing a first composition comprising water and ground corn, wherein the ground corn comprises lipase, or is sourced from GMO corn expressing lipase; inoculating the first composition with yeast and fermenting the first composition under conditions to form a second composition comprising oil; and isolating DCO from the second composition, wherein the metal ions content in the DCO is decreased by at least about 10% relative to the metal ions content in DCO produced in the absence of ground corn comprising lipase.

In some aspects, the methods above further comprise breaking an emulsion comprising corn oil and isolating the oil to obtain DCO useful as a renewable diesel feedstock containing 10 ppm, 9 ppm, 8 ppm, 7 ppm, 6 ppm, 5 ppm, 4 ppm, 3 ppm, 2 ppm, 1 ppm, etc., metal ions.

Provided herein is a composition for ethanol production comprising ground corn, water, and *S. cerevisiae*, wherein the *S. cerevisiae* is genetically modified to produce lipase. In some aspects, the *S. cerevisiae* comprises a nucleotide sequence encoding a polypeptide selected from the group consisting of SEQ ID NOs: 1-27.

Provided herein is a composition for ethanol production comprising ground corn, water, and *S. cerevisiae*, wherein the ground corn comprises lipase in an amount sufficient to reduce metal ion content in distillers corn oil. In some aspects, the ground corn is obtained from a plant which is genetically modified to express lipase.

DESCRIPTION

As used in this specification and the appended claims, the singular forms "a", "an", and "the" include plural references unless the context clearly dictates otherwise. Thus, for example, a reference to "a method" includes one or more methods, and/or steps of the type described herein and/or which will become apparent to those persons skilled in the art upon reading this disclosure and so forth.

The word "exemplary" is used to mean serving as an example, instance, or illustration. Any embodiment or design described as "exemplary" is not necessarily to be construed as preferred or advantageous over other embodiments or designs, nor is it meant to preclude equivalent exemplary structures and techniques known to those of ordinary skill in the art. Rather, use of the word exemplary is intended to present concepts in a concrete fashion, and the disclosed subject matter is not limited by such examples.

The term "or" is intended to mean an inclusive "or" rather than an exclusive "or." To the extent that the terms "comprises," "has," "contains," and other similar words are used in either the detailed description or the claims, for the avoidance of doubt, such terms are intended to be inclusive in a manner similar to the term "comprising" as an open transition word without precluding any additional or other elements.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All patents, applications and non-patent publications mentioned in this specification are incorporated herein by reference in their entireties.

Industrial fermentation involves the breakdown of a feedstock by one or more microorganisms, e.g. yeast and/or bacteria, into one or more products. In addition to the feedstock, other nutrients may be provided to the organism to facilitate the fermentation. For example, a traditional ethanol fermentation process utilizes grain-based feedstocks (e.g., corn, sorghum/milo, barley, wheat, etc.), or other sugar sources (e.g., sugar cane, sugar beets, etc.). Enzymes, whether endogenous to the grain, added to the fermenter, or produced by yeast, convert components of the feedstock into simple sugars. Yeast, acting subsequent to or simultaneously with the enzymes, convert the simple sugars to ethanol and carbon dioxide.

In a typical ethanol production plant, corn, or other suitable primary feedstock is ground for fermentation. The entire corn kernel can be ground for fermentation, or the corn kernel may be fractionated into its component parts, and only the starchy endosperm ground for use in fermentation. Any suitable feedstock, subjected to virtually any suitable pretreatment, can be used in the methods and compositions provided herein.

The ground corn or other primary feedstock may be combined with water to form a slurry, and the pH of the slurry mixture may be adjusted as needed. A microorganism, for example, a yeast such as *S. cerevisiae*, is added. The yeast is selected to provide rapid growth and fermentation rates in the presence of high temperature and high ethanol levels. The amount of yeast starter employed is selected to effectively produce a commercially significant quantity of ethanol in a suitable time, e.g., less than 75 hours or less than 88 hours.

Yeast can be added to the fermentation by any of a variety of methods known for adding yeast to fermentation processes. Other desired components can be added to the fermenter, including certain enzymes which produce monomeric sugars from polymeric sugars (e.g. glucose from starch) in the fermentable solids for simultaneous saccharification and fermentation (SSF). These enzymes can be commercially sourced, may be present in the feedstock (genetically modified corn, for example), or may be expressed by the yeast. Exemplary enzymes include glucoamylase and alpha-amylase. Alternatively, saccharification can be performed separate from fermentation.

In some aspects, a fermenter contains a solids concentration of about 20% to about 50%, for example about 30% to about 40%, about 31%, about 32%, about 33%, about 34%, or about 35%. Maintaining overall fermenter solids concentrations within a specified range is useful for maximizing fermentability and ethanol production.

The slurry can be held at specified temperatures to facilitate the production of ethanol for a determined period of time. Fermenting can include contacting a mixture including sugars from the reduced plant material (e.g., fractionated plant material) with yeast under conditions suitable for growth of the yeast and production of ethanol. During fermentation, the yeast converts the sugars (e.g. glucose) to ethanol and carbon dioxide, and between the enzymatic production of sugars (e.g. glucose) and the fermentation process, sugars (e.g. glucose) may be maintained in the system at a low steady state. After fermentation, further treatment and/or distillation is performed to recover the ethanol, distillers corn oil (DCO), carbon dioxide, dried distillers grains (DDG), and/or other co-products.

The term "DCO" can be used generically to describe the oil co-product of a corn-to-ethanol process, including the oil present in, e.g., an emulsion in stillage and the isolated oil obtained by separating the oil from aqueous components of stillage, e.g., by breaking an emulsion and separating the aqueous phase. As used herein, DCO is the resulting corn oil after it has been recovered from the aqueous components.

DCO may contain levels of metal content ($Na^+$, $K^+$, $Mg^{2+}$, $Ca^{2+}$, etc.), which are detrimental to downstream processes. For example, metals in DCO may deactivate catalysts used in making renewable diesel.

The term "crude DCO" refers to distillers corn oil which has not been subjected to a refining process, i.e., distillation, deodorization, bleaching, etc. Refining can include a water or acid degumming step or chemical refining. The resulting gums or soap stock can be removed by centrifugation and/or other separation technology. These methods can be performed alone or in combination with a bleaching step to act as a pretreatment step to facilitate removal of metals from the oil prior to conversion to renewable diesel. The refining process can also lower the free fatty acid content (FFA), the moisture content, the insolubles content and/or the unsaponifiables content.

Triglycerides are the main constituent of vegetable fat and are esters having a glycerol backbone with three fatty acids attached to it. Similarly, diglycerides and monoglycerides are esters of glycerol with two and one fatty acids linked, respectively. Fatty acids may be separated from the glycerol backbone to become non-esterified fatty acids, i.e. free fatty acids (FFAs), such that a vegetable oil, depending on its source and processing, may have from a relatively low level to a relatively high level of FFAs; e.g. from 0 to greater than 20% FFA. As used herein, the term FFA refers to an unesterified fatty acid, or more specifically, a fatty acid having a carboxylic acid head and a saturated or unsaturated unbranched aliphatic tail (group) of about 4 to about 28 carbons. FFAs may be esterified with other alcohols to form a fatty acid ester. For example, a fatty acid methyl ester (FAME) is fatty acid esterified with methanol and a fatty acid ethyl ester (FAEE), is a fatty acid esterified with ethanol.

It has been determined and disclosed herein that addition of an endogenous esterase, i.e. an esterase-producing microorganism, to propagation and/or fermentation (including a side-tank propagation) can be beneficial to recovery of DCO having decreased metal ion content. As such, provided herein are compositions, methods, and systems for propagation and fermentation utilizing an esterase-producing microorganism.

While not wishing to be bound by theory, it is thought that fermentation with endogenous esterase, e.g. lipase, reduces metal ion content by decreasing FFA content and increasing FAEE content of the corn oil. The reduction in FFA reduces the opportunity for metal soaps to form e.g. when pH is increased during biorefinery processes e.g. when breaking an emulsion to separate corn oil from an aqueous stream. Some of these metal soaps will segregate with the oil during centrifugation. By limiting soap formation, fewer soaps, and thus fewer metal ions, segregate with the oil resulting in a lower metals content in the oil. The metal ions are instead dissolved in the aqueous stream and cleanly separate from the oil during centrifugation.

A yeast or bacteria that naturally produces lipase can be used in the methods, systems, and compositions provided herein. However, a yeast or bacteria can be genetically engineered to produce lipase. Exemplary bacteria which can be engineered to produce lipase include, but are not limited to *Escherichia coli, Bacillus* spp (several species), and *Pseudomonas* spp (several species). Exemplary yeast which can be engineered to produce lipase include, but are not limited to, *Candida boidinii, Pichia pastoris*, and *Saccharomyces cerevisiae*. Yeast or bacteria can be genetically engineered to produce an esterase, for example, a lipase according to any one of SEQ ID NOs: 1-27. Promoters are chosen which control the level of the enzyme produced by the cell, and in this case, tightly regulated or low expressing promotors are chosen to maintain esterase production at the desired level necessary to achieve a decreased metal ion content in the DCO.

In some embodiments, the esterase is a newly engineered enzyme with a lower catalytic efficiency. In some embodiments, the esterase is a newly engineered enzyme with a cholesterol esterase backbone. Such enzymes have lower efficiency than typical commercially available esterases permitting lower levels of esterase production in a system optimized for ethanol production.

As used herein, certain esterases are useful in reducing metal ion content in DCO. Exemplary esterases include lipases.

In certain embodiments, the method utilizes an esterase defined by EC 3.1.1.1 (a carboxylic-ester hydrolase) or EC 3.1.1.3 (a triacylglycerol lipase). A yeast or bacteria can be genetically modified to produce carboxylic-ester hydrolase or triacylglycerol lipase.

In certain embodiments, the method utilizes a CALB lipase. A yeast or bacteria can be genetically modified to produce CALB lipase. Unlike some general lipases, the CALB lipase, as well as some cholesterol esterases, favor the production of FAEE versus FFA production.

Fermentation in the presence of a microorganism that produces a low level of active CALB lipase reduces the metal concentration in DCO by at least about 20% to 90%, for example, by about 20%, 30%, 40%, 50%, 60%, 70%, 80%, or 90%. In some aspects, the metal concentration can be reduced to below 10 ppm.

The metal concentration of DCO can be further reduced through post processes such as water degumming as described in U.S. Patent Application 2019/0376002.

Fermentation conditions for commercial ethanol production are different from those conditions optimized to produce enzymes such as esterases. Typically, growth of an organism for the purpose of producing enzyme commercially focuses on conditions for producing a cleaner less variable enzyme stream as fast and high in enzyme quantity as possible. For example, conditions for growth of an enzyme-producing yeast include low solids content (6% or below) in the growth media, a mid-range pH 5-7 (depending on the organism), a temperature around 30° C., with excess nutrients, in an aerobic system. Yeasts grown for enzyme production are typically sensitivity to a high ethanol titer, so growth conditions are manipulated to minimize ethanol production.

In contrast, conditions for commercial ethanol production include longer fermentation times, for example, up to 90 hours, high solids content of the fermentation broth (between 20% and 50%), a pH of about 4.0 to 5.0, a temperature of about 30° C. to 35° C., e.g. about 32° C. to about 34° C., in an anaerobic system. Lipase producing microorganisms when present in a commercial ethanol fermentation are not in optimal enzyme producing conditions, and thus the amount of lipase is regulated such that the concentration is at a level sufficient to achieve decreased metal content of DCO, but not high enough to increase FFA and/or metal content of DCO.

Long-chain lipase units (LCLU) refers to the standard units for measuring lipase activity and are described in patent application, WO 2015181308 A1. Such units can be measured by detecting the hydrolysis product, p-nitrophenol (PNP), of PNP-palmitate and measuring its resulting absorbance at 405 nm. 1 unit is defined as the amount of enzyme to release 1 μmol of PNP per minute. However, as used herein, the amount of lipase produced during propagation and/or fermentation was based upon Lipase Unit (LU) equivalency, e.g. where the lipase produced is present in the fermentation in an amount equivalent to about 0.03 to about 0.70 LU/g dry solids (DS), or about 0.01 to about 1.00 LU/g dry solids; where the lipase produced is present in the fermentation in an amount from about 0.0006% to about 0.0150% w/w DS, or from about 0.0001% to about 0.030% w/w DS; where the lipase produced is present in the fermentation in an amount from about 0.02% to about 0.5% w/w corn oil, or from about 0.01% to about 1.0% w/w corn oil; or where the lipase produced is present in the fermentation in an amount from about 5 L to about 100 L in a 550,000 gal fermentation vat.

In some aspects, a lipase producing microorganism will generate about 0.15 to about 0.3 lipase units (LU) per gram of dry solids in the early stages of fermentation or during propagation in order to decrease metal content in the DCO.

In other aspects, the lipase produced by the esterase-producing microorganism is present in an amount sufficient to achieve decreased levels of FFA, for example, at least a 10% reduction in FFA levels, at least a 20% reduction in FFA levels, at least a 30% reduction in FFA levels, at least a 40% reduction in FFA levels, at least a 50% reduction in FFA levels, or at least a 75% reduction in FFA levels in crude DCO relative to a fermentation in the absence of an esterase-producing microorganism. In some aspects, the methods provided herein result in crude DCO having an FFA content of less than about 5%, about 4%, about 3%, about 2%, or about 1% by weight.

In other aspects, the lipase produced by the esterase-producing microorganism is present in an amount sufficient to achieve increased levels of FAEE, for example, at least a 10% increase in FAEE levels, at least a 20% increase in FAEE levels, at least a 30% increase in FAEE levels, at least a 40% increase in FAEE levels, at least a 50% increase in FAEE levels, or at least a 75% increase in FAEE levels in crude DCO relative to a fermentation in the absence of an esterase-producing microorganism. In some aspects, the methods provided herein result in crude DCO having an FAEE content of more than about 12%, about 15%, about 20%, about 25%, or about 30% by weight.

Likewise, the lipase produced by the esterase-producing microorganism is present in an amount sufficient to achieve decreased levels of metal, i.e. metal ion content, for example, at least about 10% to about 100% decrease in metal, i.e., at least about 20% to about 90%, at least about 30% to about 100%, at least about 40% to about 60%, at least about 50% to about 90%, etc., or at least about a 10% decrease in metal, at least about a 20% decrease in metal, at least about a 30% decrease in metal, at least about a 40% decrease in metal, at least about a 50% decrease in metal, at least about a 60% decrease in metal, at least about a 70% decrease in metal, at least about an 80% decrease in metal, or at least about a 90% decrease in metal in DCO relative to a DCO obtained from fermentation in the absence of an esterase-producing microorganism. While the decrease in metal, e.g. metal ions content, correlates with reduced FFA/increased FAEE, the correlation is not proportionate, and a small change in FFA/FAEE can substantially alter metal content in DCO.

In some aspects, the metals content in DCO produced according to the methods and compositions provided herein is less than about 10 ppm, or less than about 7 ppm, or less than about 5 ppm, or less than about 4 ppm, or 3 ppm, or 2 ppm, or 1 ppm.

In some embodiments, DCO is obtained by separating the corn oil from fermentation residue (e.g. stillage, thin stillage, or syrup) to provide an emulsion layer and a first aqueous layer. The corn oil is present in the emulsion layer and can be isolated from the emulsion by breaking the emulsion to provide a corn oil phase and an aqueous phase. The emulsion may be broken by addition of an emulsion breaking chemical such as a demulsifier or a polysorbate. The emulsion may be broken by adjusting the pH of the emulsion layer to a range of about pH 6.0 to 9.0, or about 7.0 to 8.0. Once the emulsion is broken, the corn oil phase is separated from the aqueous phase to provide the isolated DCO. Separating can be accomplished centrifugation or by simply allowing the phase separation to occur over time and decanting. In some aspects, the metals content in a renewable diesel feedstock extracted from a broken emulsion, i.e. the DCO obtained according to the methods and compositions provided herein, is reduced by at least about 50%, or by about 10% to about 90%, relative to the metals content in DCO obtained without the use of endogenous lipase. In some aspects, the metals content is less than about 10 ppm, or less than about 7 ppm, or less than about 5 ppm, or less than about 4 ppm, or 3 ppm, or 2 ppm, or 1 ppm. In some aspects, the FFA content in the produced DCO produced according to the methods and compositions provided herein is less than about 5%. In some aspects, the FAEE content in the DCO produced according to the methods and compositions provided herein is greater than about 12%, for example is greater than about 15%, about 20%, about 25%, or about 30%.

In some aspects, the lipase produced by the esterase-producing microorganism, or the lipase present in the ground corn, is present in the fermentation in an amount to achieve esterification of FFA; is present in the fermentation in an amount sufficient to achieve decreased FFA in DCO, for example, about 10% to about 50% less FFA relative to a fermentation in the absence of endogenous lipase; is present in the fermentation in an amount sufficient to achieve decreased metal content in the DCO, for example, at least about a 10% decrease in metal, at least about a 20% decrease in metal, at least about a 30% decrease in metal, at least about a 40% decrease in metal, or at least about a 50% decrease in metal, or more, relative to a fermentation in the absence of endogenous lipase.

In some aspects, the lipase produced in propagation or fermentation generates esters, determined by FAEE increase, and decreases FFA acid in the system. This shift correlates to the reduction in metals. In some aspects, the increase in FAEE is about 5% to about 30%, for example, about 15% to about 20%, and a decrease in FFA to about 5% to about 3%. In other words, the endogenous lipase effects an esterification of the FFA in the system as measured by the increase in FAEE content in the DCO.

Lipase activity in a given system can be measured by obtaining a ratio of FFA to FAEE at various timepoints during propagation or fermentation, relative to the ratio of FFA to FAEE at the start of the propagation or fermentation, or time zero.

Other assays used to measure endogenous lipase activity can be modified to suit the purposes herein and are known to those skilled in the art.

EXAMPLES

The following examples are provided for illustrative purposes only and are not intended to limit the scope of the invention.

Example 1

Fermenting in the presence of a lipase (AKA esterase, E.C. 3.1.1.3) decreases the level of FFA by esterifying the FFA with ethanol to form FAEE. Lipases similar to the Lipozyme CALB L lipase (i.e. with high sequence identity) preferentially perform the reaction over hydrolysis and/or transesterification of triglycerides.

In the present example, lipase was added at the beginning of bench-scale fermentations at varying levels. After approximately 90 hours of fermentation to form a beer, an emulsion was isolated from the beer by centrifugation. The oil was solvent extracted from the emulsion using chloroform. The solvent was evaporated, and the corresponding FAEE content was determined by an in-house GC-FID method and the FFA was determined by a method similar to AOCS Ca 5a-40.

The resulting corn oil compositions exhibit dose dependent reduction in FFA content, which correlates to a reduced metal ion content.

TABLE 1

Lipozyme CALB L lipase enzyme approximate dosing and corresponding emulsion FAEE and FFA content.

| LU/g DS[a] | % w/w DS | % w/w Corn Oil | L/550,000 gal Ferm | % FAEE (% w/w)[b] | FFA (% w/w)[b] |
|---|---|---|---|---|---|
| 0 | 0% | 0% | 0 | 13.0% | 17.9% |
| 0.03 | 0.0006% | 0.02% | 5 | 18.6% | 14.1% |
| 0.06 | 0.0013% | 0.04% | 10 | 21.3% | 10.6% |
| 0.32 | 0.0065% | 0.20% | 50 | 29.3% | 4.3% |
| 0.65 | 0.0130% | 0.40% | 100 | 31.2% | 3.9% |

[a]Lipase Unit (LU), Dry Solids (DS) - 1 LU, quantity of enzyme to produce 1 μmol of butyric acid from tributyrin
[b]FFA and FAEE content of oil solvent extracted from the emulsion FFA content can be correlated to the metal soap content in (DCO). When breaking an oil water emulsion in a stillage stream by increasing the pH (e.g., with sodium hydroxide) to pH 7 or pH 8, one or more metal soaps can be formed. The increase in pH drives deprotonation of FFA forming a salt between fatty acid carboxylate with existing cationic metals ($Na^+$, $K^+$, $Mg^{2+}$, $Ca^{2+}$, etc.). Therefore, by reducing the level of FFA in the emulsion, the amount of metal soaps formed can also be reduced resulting in less carryover into the DCO during separation. In addition, the presence of FAEE can decrease the viscosity of the DCO improving corn oil extraction or additional separations carried out to further reduce DCO metal content.

Example 2

FFA and metals content were shown to decrease in DCO produced in plant scale fermentation with varying amounts of lipase added during fermentation. Lipase was added at the beginning of plant-scale fermentation, to reflect endogenously produced lipase, at varying levels. The oil was isolated at the plant by previously described methodologies.

The FAEE and FFA content of the DCO was determined as previously described. Total phosphorous and metals (Ca, Cu, Fe, Mg, Mn, K, P, Na, S, and Zn) were determined by AOAC 2014.11.

The data in Table 2 shows FFA content of oil extracted from fermentation with or without lipase at varying levels. DCO FFA content can be determined by test method AOCS Ca 5a-40.

TABLE 2

Effect of Exogenous Lipase Enzyme Dosing on FFA and Total Phosphorus and Metals

| Lipase Dose (L/550,000 gal) | Lipase Name | Approximate Fermentation pH | Approximate Fermentation Hours | % FFA in Oil | Total Phosphorous and Metals PPM |
|---|---|---|---|---|---|
| 0 | NA | 4.3 | 80 | 7.3% | 276 |
| 5 | Lipozyme CALB L | 4.3 | 80 | 4.2% | 57 |
| 0 | NA | 4.6 | 90 | 4.8% | 224 |
| 3 | Lipozyme CALB L | 4.6 | 90 | 3.8% | 51 |

Example 3

A fermentation vat containing ground corn and water is inoculated with an ethanologen, *S. cerevisiae*, and a bacteria engineered to produce a lipase having the amino acid sequence of SEQ ID NO: 1. The yeast is added to the fermentation during the fermenter fill at a rate of 5 to 100 pounds of active dry yeast (ADY) per 100,000 gallons of fermentation mash. The bacteria are added to the fermentation for production of lipase in an amount sufficient to decrease metal ion content in the resulting DCO by at least about 20% relative to a fermentation carried out in the absence of a lipase producing bacteria. Fermentation proceeds over 74-88 hours, producing a commercially significant quantity of ethanol in that time.

DCO is obtained by separating the corn oil from fermentation residue to provide an emulsion layer and a first aqueous layer and breaking the emulsion layer by adjusting the pH to about pH 8 to provide a corn oil layer and a second aqueous layer. The corn oil layer is separated from the second aqueous layer to provide the isolated DCO composition. Separating can be accomplished by simply allowing the phase separation to occur over time and decanting or centrifuging to isolate the oil layer. Metal ion content in the produced DCO is assessed and found to be decreased by 20% relative to the control (DCO obtained from a similar fermentation in the absence of endogenous lipase).

Example 4

Yeast can be propagated, acclimated, and conditioned by incubating the yeast in a prefermenter or propagation tank. In this experiment, feedstock is inoculated with about 5 to 50 pounds of yeast per 10,000 gallon volume of fermenter volume in a prefermenter or propagation tank. The yeast is engineered to express lipase. Incubation proceeds over a time period of 16 hours during the propagation stage, which is aerated to encourage yeast growth. The prefermenter used to inoculate the main fermenter is about 10% by volume the capacity of the main fermenter. After propagation, the yeast cells are lysed, and the lysate is added to a fermentation tank along with a yeast ethanologen. Fermentation is carried out under conditions optimized for commercial ethanol production. After an 88 hour fermentation, ethanol is distilled from the beer and DCO is isolated from the stillage. Metal ion content in the DCO is assessed and found to be decreased by 80% relative to the control (DCO obtained from a similar fermentation in the absence of endogenous lipase).

Example 5

In this experiment, feedstock is inoculated with About 5 to 50 pounds of yeast per 10,000 gallon volume of fermenter volume in a prefermenter or propagation tank. The yeast is engineered to express lipase. Incubation proceeds over a time period of 12 hours during the propagation stage, which is aerated to encourage yeast growth and lipase production. The prefermenter used to inoculate the main fermenter is about 10% by volume the capacity of the main fermenter. After propagation, the yeast cells are added to a fermentation tank. Fermentation is carried out under conditions optimized for commercial ethanol production. After a 70 hour fermentation, ethanol is distilled from the beer and DCO is isolated from the stillage. Metal ion content in the DCO is assessed and found to be decreased by 50% relative to the control (DCO obtained from a similar fermentation in the absence of endogenous lipase).

Example 6

In this experiment, genetically modified ground corn engineered to produce lipase is inoculated with an ethanologen for commercial production of ethanol. The ethanologen is added to the fermentation during the fermenter fill at a rate of 100 pounds of active dry yeast (ADY) per 100,000 gallons of fermentation mash. Fermentation proceeds over 74-88 hours, producing a commercially significant quantity of ethanol in that time. After fermentation, ethanol is distilled from the beer and DCO is isolated from the stillage. Metal ion content in the isolated DCO is assessed and found to be decreased by 55% relative to the control (DCO obtained from a similar fermentation in the absence of endogenous lipase).

Example 7

In this experiment, ground corn is mixed with water and cooked to liquefy starch. The cooked slurry is transferred to a fermenter where it is mixed with yeast and lipase. Fermentation is carried out under conditions optimized for commercial ethanol production. After a 75 hour fermentation, ethanol is distilled from the beer and DCO is isolated from the stillage. Metal ion content in the DCO assessed and found to be decreased by 50% relative to the control (DCO obtained from a similar fermentation in the absence of endogenous lipase).

Further Examples

1. A method of producing distillers corn oil (DCO), the method comprising:
(a) inoculating a feedstock:
(i) with a combination of a first microorganism which is an ethanologen and a second microorganism for producing lipase;
(ii) with an ethanologen, wherein the ethanologen is a yeast genetically modified to produce lipase; or
(iii) with an ethanologen, wherein the feedstock contains starch from a genetically modified plant engineered to produce lipase; and (b) fermenting the feedstock to produce ethanol and DCO.
2. The method of example 1, wherein the step of (a)(i) includes inoculating a feedstock in a propagation tank or a fermentation tank with the ethanologen and the second microorganism.
3. The method of example 1, wherein the step of (a)(i) includes inoculating a feedstock in a first propagation tank with the ethanologen and inoculating a feedstock in a second propagation tank (side tank propagation) with the second microorganism, and wherein step (b) further comprises fermenting contents obtained from the first propagation tank with contents obtained from a second propagation tank in the presence of feedstock for ethanol production.
4. The method of example 1, wherein the step of (a)(i) includes inoculating a feedstock in a fermentation tank with the ethanologen and inoculating a feedstock in a propagation tank (side tank propagation) with the second microorganism, and wherein step (b) further comprises adding the contents obtained from the propagation tank to the fermentation tank and fermenting feedstock for ethanol production.
5. The method of example 1, wherein the DCO exhibits decreased levels of cationic metals ($Na^+$, $K^+$, $Mg^{2+}$, $Ca^{2+}$, etc.) or phosphorus relative to the levels of cationic metals or phosphorus present in DCO produced in the absence of a lipase-producing microorganism, yeast, or plant.
6. The method of example 1, wherein the DCO exhibits decreased soap content relative to the soap content in DCO produced in the absence of a lipase-producing microorganism, yeast, or plant.
7. The method of example 1, wherein the DCO exhibits decreased viscosity relative to the viscosity of a DCO produced in the absence of a lipase-producing microorganism, yeast, or plant.
8. The method of example 1, wherein the DCO comprises increased FAEE/decreased FFA relative to the FAEE/FFA content of a DCO produced in the absence of a lipase-producing microorganism, yeast, or plant.
9. The method of example 1, wherein the lipase produced is present in the fermentation in an amount equivalent to about 0.01 to about 1.00 LU/g dry solids (DS); about 0.0001% to about 0.0300% w/w DS; about 0.02% to about 0.5% w/w corn oil; or about 1 L to about 100 L in a 550,000 gal fermentation vat.
10. The method of example 1, wherein the lipase produced is present in an amount sufficient to reduce metal ion content or phosphorus content in DCO by at least about 20% relative to a fermentation in the absence of a lipase-producing microorganism, yeast, or plant.
11. The method of example 1, wherein the lipase produced is present in an amount sufficient to reduce metal ion content or phosphorus content in DCO by at least about 50% relative to a fermentation in the absence of a lipase-producing microorganism, yeast, or plant.
12. The method of example 1, wherein the lipase produced is present in the fermentation in an amount sufficient to reduce FFA content in DCO to less than about 15% w/w relative to a fermentation in the absence of a lipase-producing microorganism, yeast, or plant.
13. The method of example 1(a)(i), wherein the ethanologen is S. cerevisiae and the second microorganism is a genetically modified yeast engineered to produce lipase, and wherein the lipase produced by the second yeast is present in the fermentation in an amount sufficient to reduce metal ion content or phosphorus content in DCO by at least about 10% relative to a fermentation in the absence of a lipase-producing microorganism, yeast, or plant.

14. The method of example 1(a)(i), wherein the ethanologen is *S. cerevisiae* and the second microorganism is a bacteria engineered to produce lipase, and wherein the lipase produced by the bacteria is present in the fermentation in an amount sufficient to reduce metal ion content or phosphorus content in DCO by at least about 10% relative to a fermentation in the absence of a lipase-producing microorganism, yeast, or plant.

15. The method of example 1(a)(ii), wherein the yeast is *S. cerevisiae* and the lipase produced by the yeast is present in the fermentation in an amount equivalent to about 0.03 to about 0.70 LU/g dry solids (DS).

16. A composition comprising two microorganisms, wherein the first microorganism is an ethanologen which is a yeast strain and the second microorganism is a yeast strain or bacteria genetically modified to produce lipase under one or more conditions for ethanol production; wherein one or more conditions for ethanol production are selected from the group consisting of: (i) anaerobic fermentation; (ii) fermentation solids content of at least about 20%; (iii) a pH of about 4.0 to about 5.0; and (iv) a temperature of about 37° C.

17. The composition of example 16, wherein the ethanologen is *S. cerevisiae*.

18. The composition of example 16, wherein the second microorganism is a bacteria.

19. The composition of example 16, wherein the second microorganism is a yeast strain.

20. A fermenter comprising the composition of example 16, water, and feedstock.

21. A method of producing DCO as a by-product of fermentation associated with ethanol production, the method comprising: (a) inoculating a feedstock with a combination of two yeast strains, wherein the first yeast strain is an ethanologen and the second yeast strain produces lipase; and (b) fermenting the feedstock to produce ethanol and DCO, wherein the metal ion content or phosphorus content in the emulsion is decreased by at least about 10% relative to a DCO obtained as the by-product of fermentation in the absence of a lipase producing yeast.

22. The method of example 21, wherein the ethanol titer after fermentation is unchanged relative to the same fermentation performed in the absence of the lipase expressing yeast strain.

23. A method of producing DCO, comprising:

providing a first composition comprising water and ground corn;

inoculating the first composition with: (i) a combination of an ethanologen, which is a first yeast for fermentation of the ground corn, and a second yeast engineered to produce lipase; or (ii) an ethanologen which is genetically modified to produce lipase;

fermenting the composition under conditions to form a second composition comprising DCO, wherein the lipase produced is sufficient to reduce metal ion content or phosphorus content in the resulting DCO.

24. A method of producing DCO, comprising:

providing a first composition comprising water and ground corn, wherein the ground corn comprises lipase, or is sourced from GMO corn expressing lipase;

inoculating the first composition with yeast; and fermenting the first composition under conditions to form a second composition comprising DCO.

25. The method of example 23 or example 24, further comprising isolating an emulsion comprising DCO; breaking the emulsion comprising the DCO; and isolating the DCO to obtain a renewable diesel feedstock containing less than about 10 ppm metal ions.

26. A composition for ethanol production comprising ground corn, water, and *S. cerevisiae*, wherein the *S. cerevisiae* is genetically modified to produce lipase, and wherein the ground corn is present in the composition in an amount of about 20% to 50% by weight solids.

27. The composition of example 26, wherein the *S. cerevisiae* comprises a nucleotide sequence encoding a polypeptide selected from the group consisting of SEQ ID NOS: 1-27.

28. The composition of example 26, wherein the lipase is produced in an amount sufficient to reduce metal ion content or phosphorus content in DCO.

29. A composition for ethanol production comprising ground corn, water, and *S. cerevisiae*, wherein the ground corn comprises lipase in an amount sufficient to reduce metal ion content or phosphorus content in distillers corn oil.

30. The composition of example 29, wherein the ground corn is genetically modified to express lipase.

31. A method of producing DCO, comprising fermenting feedstock in presence of an esterase or lipase, wherein the DCO exhibits at least about a 10% to about 100% reduction in metal ion content or phosphorus content relative to a DCO produced in the absence of an esterase or lipase.

32. The method of example 31, wherein the esterase or lipase is present in an amount sufficient to reduce metal ion content or phosphorus content in DCO by at least about 50% relative to a fermentation in the absence of esterase or lipase.

33. The method of example 31, wherein the esterase or lipase is present in an amount sufficient to reduce metal ion content or phosphorus content in DCO by at least about 80% relative to a fermentation in the absence of esterase or lipase.

34. The method of example 31, wherein the metal ion is selected from the group consisting of $Na^+$, $K^+$, $Mg^{2+}$, $Ca^{2+}$.

35. The method of example 31, wherein the phosphorus content is reduced.

While the invention has been particularly shown and described with reference to a number of embodiments, it would be understood by those skilled in the art that changes in the form and details may be made to the various embodiments disclosed herein without departing from the spirit and scope of the invention and that the various embodiments disclosed herein are not intended to act as limitations on the scope of the claims.

What is claimed is:

1. A method of producing distillers corn oil (DCO), the method comprising:
(a) inoculating a feedstock:
(i) with a combination of a first microorganism which is an ethanologen and a second microorganism genetically engineered to produce esterase; or
(ii) with an ethanologen, wherein the ethanologen is a yeast genetically modified to produce esterase; and
(b) fermenting the feedstock in the presence of produced esterase to produce ethanol and DCO,
wherein the esterase is present in an amount sufficient to reduce (i) free fatty acid (FFA) content and (ii) metal ion content or phosphorus content, in DCO,
wherein the DCO comprises decreased FFA content relative to the FFA content of a DCO produced in the absence of an esterase-producing microorganism or genetically modified yeast; and
wherein the metal ion content or phosphorus content is reduced by at least about 10% relative to fermentation in the absence of an esterase-producing microorganism or genetically modified yeast.

2. The method of claim 1, wherein the step of (a)(i) includes inoculating a feedstock in a propagation tank or a fermentation tank with the ethanologen and the second microorganism.

3. The method of claim 1, wherein the DCO exhibits decreased levels of cationic metals (Na+, K+, Mg2+, Ca2+, etc.) or phosphorus relative to the levels of cationic metals or phosphorus present in DCO produced in the absence of an esterase-producing microorganism or yeast.

4. The method of claim 1, wherein the DCO exhibits decreased soap content relative to the soap content in DCO produced in the absence of an esterase-producing microorganism or yeast.

5. The method of claim 1, wherein the DCO exhibits decreased viscosity relative to the viscosity of a DCO produced in the absence of an esterase-producing microorganism or yeast.

6. The method of claim 1, wherein the DCO comprises increased FAEE relative to the FAEE content of a DCO produced in the absence of an esterase-producing microorganism or yeast.

7. The method of claim 1, wherein the esterase produced is present in the fermentation in an amount equivalent to about 0.01 to about 1.00 LU/g dry solids (DS); about 0.0001% to about 0.0300% w/w DS; about 0.02% to about 0.5% w/w corn oil; or about 1 L to about 100 L in a 550,000 gal fermentation vat.

8. The method of claim 1, wherein the esterase produced is present in an amount sufficient to reduce metal ion content or phosphorus content in DCO by at least about 20% relative to a fermentation in the absence of an esterase-producing microorganism or yeast.

9. The method of claim 1, wherein the esterase produced is present in an amount sufficient to reduce metal ion content or phosphorus content in DCO by at least about 50% relative to a fermentation in the absence of an esterase-producing microorganism or yeast.

10. The method of claim 1, wherein the esterase produced is present in the fermentation in an amount sufficient to reduce FFA content in DCO to less than about 15% w/w relative to a fermentation in the absence of an esterase-producing microorganism or yeast.

11. The method of claim 1(a)(i), wherein the ethanologen is *S. cerevisiae* and the second microorganism is a genetically modified yeast engineered to produce esterase.

12. The method of claim 1(a)(i), wherein the ethanologen is *S. cerevisiae* and the second microorganism is a bacteria engineered to produce esterase.

13. The method of claim 1(a)(ii), wherein the yeast is *S. cerevisiae* and the esterase produced by the yeast is present in the fermentation in an amount equivalent to about 0.03 to about 0.70 LU/g dry solids (DS).

14. The method of claim 1, wherein the esterase is a carboxylic-ester hydrolase.

15. The method of claim 1, wherein the esterase is a carboxylic esterase.

16. The method of claim 1, wherein the esterase is a lipase.

17. The method of claim 16, wherein the lipase is a CALB lipase.

18. The method of claim 16, wherein the lipase is a triacylglycerol lipase.

* * * * *

SEQUENCE LISTING

```
Sequence total quantity: 27
SEQ ID NO: 1              moltype = AA   length = 327
FEATURE                  Location/Qualifiers
REGION                   1..327
                         note = Synthetic
source                   1..327
                         mol_type = protein
                         organism = synthetic construct
SEQUENCE: 1
MALPSGSDPA FSQPKSVLDA GLTCQGASPS SVSKPILLVP GTGTTGPQSF DSNWIPLSTQ    60
LGYTPCWISP PPFMLNDTQV NTEYMVNAIT ALYAGSGNNK LPVLTWSQGG LVAQWGLTFF   120
PSIRSKVDRL MAFAPDYKGT VLAGPLDALA VSAPSVWQQT TGSALTTALR NAGGLTQIVP   180
TTNLYSATDE IVQPQVSNSP LDSSYLFNGK NVQAQAVCGP LFVIDHAGSL TSQFSYVVGR   240
SALRSTTGQA RSADYGITDC NPLPANDLTP EQKVAAAALL APAAAAIVAG PKQNCEPDLM   300
PYARPFAVGK RTCSGIVTPL EHHHHHH                                       327

SEQ ID NO: 2              moltype = AA   length = 342
FEATURE                  Location/Qualifiers
REGION                   1..342
                         note = Synthetic
source                   1..342
                         mol_type = protein
                         organism = synthetic construct
SEQUENCE: 2
MKLLSLTGVA GVLATCVAAT PLVKRLPSGS DPAFSQPKSV LDAGLTCQGA SPSSVSKPIL    60
LVPGTGTTGP QSFDSNWIPL STQLGYTPCW ISPPPFMLND TQVNTEYMVN AITALYAGSG   120
NNKLPVLTWS QGGLVAQWGL TFFPSIRSKV DRLMAFAPDY KGTVLAGPLD ALAVSAPSVW   180
QQTTGSALTT ALRNAGGLTQ IVPTTNLYSA TDEIVQPQVS NSPLDSSYLF NGKNVQAQAV   240
CGPLFVIDHA GSLTSQFSYV VGRSALRSTT GQARSADYGI TDCNPLPAND LTPEQKVAAA   300
ALLAPAAAAI VAGPKQNCEP DLMPYARPFA VGKRTCSGIV TP                      342

SEQ ID NO: 3              moltype = AA   length = 339
FEATURE                  Location/Qualifiers
REGION                   1..339
                         note = Synthetic
source                   1..339
                         mol_type = protein
                         organism = synthetic construct
SEQUENCE: 3
MKYLLPTAAA GLLLLAAQPA MALPSGSDPA FSQPKSVLDA GLTCQGASPS SVSKPILLVP    60
GTGTTGPQSF DSNWIPLSTQ LGYTPCWISP PPFMLNDTQV NTEYMVNAIT ALYAGSGNNK   120
LPVLTWSQGG LVAQWGLTFF PSIRSKVDRL MAFAPDYKGT VLAGPLDALA VSAPSVWQQT   180
TGSALTTALR NAGGLTQIVP TTNLYSATDE IVQPQVSNSP LDSSYLFNGK NVQAQAVCGP   240
LFVIDHAGSL TSQFSYVVGR SALRSTTGQA RSADYGITDC NPLPANDLTP EQKVAAAALL   300
APAAAAIVAG PKQNCEPDLM PYARPFAVGK RTCSGIVTP                          339

SEQ ID NO: 4              moltype = AA   length = 326
FEATURE                  Location/Qualifiers
REGION                   1..326
                         note = Synthetic
source                   1..326
                         mol_type = protein
                         organism = synthetic construct
SEQUENCE: 4
ALPSGSDPAF SQPKSVLDAG LTCQGASPSS VSKPILLVPG TGTTGPQSFD SNWIPLSTQL    60
GYTPCWISPP PFMLNDTQVN TEYMVNAITA LYAGSGNNKL PVLTWSQGGL VAQWGLTFFP   120
SIRSKVDRLM AFAPDYKGTV LAGPLDALAV SAPSVWQQTT GSALTTALRN AGGLTQIVPT   180
TNLYSATDEI VQPQVSNSPL DSSYLFNGKN VQAQAVCGPL FVIDHAGSLT SQFSYVVGRS   240
ALRSTTGQAR SADYGITDCN PLPANDLTPE QKVAAAALMA PAAAAIVAGP KQNCEPDLMP   300
YARPFAVGKR TCSGIVTPLE HHHHHH                                        326

SEQ ID NO: 5              moltype = AA   length = 328
FEATURE                  Location/Qualifiers
REGION                   1..328
                         note = Synthetic
source                   1..328
                         mol_type = protein
                         organism = synthetic construct
SEQUENCE: 5
MADDDDDLPS GSDPAFSQPK SVLDAGLTCQ GASPSSVSKP ILLVPGTGTT GPQSFDSNWI    60
PLSTQLGYTP CWISPPPFML NDTQVNTEYM VNAITALYAG SGNNKLPVLT WSQGGLVAQW   120
GLTFFPSIRS KVDRLMAFAP DYKGTVLAGP LDALAVSAPS VWQQTTGSAL TTALRNAGGL   180
TQIVPTTNLY SATDEIVQPQ VSNSPLDSSY LFNGKNVQAQ AVCGPLFVID HAGSLTSQFS   240
YVVGRSALRS TTGQARSADY GITDCNPLPA NDLTPEQKVA AAALLAPAAA AIVAGPKQNC   300
EPDLMPYARP FAVGKRTCSG IVTPIEGR                                      328

SEQ ID NO: 6              moltype = AA   length = 342
FEATURE                  Location/Qualifiers
```

-continued

```
REGION                      1..342
                            note = Synthetic
source                      1..342
                            mol_type = protein
                            organism = synthetic construct
SEQUENCE: 6
MKLLSLTGVA GVLATCVAAT PLVKRLPSGS DPAFSQPKSV LDAGLTCQGA SPSSVSKPIL    60
LVPGTGTTGP QSFDSNWIPL SAQLGYTPCW ISPPPFMLND TQVNTEYMVN AITALYAGSG   120
NNKLPVLTWS QGGLVAQWGL TFFPSIRSKV DRLMAFAPDY KGTVLAGPLD ALAVSAPSVW   180
QQTTGSALTT ALRNAGGLTQ IVPTTNLYSA TDEIVQPQVS NSPLDSSYLF NGKNVQAQAV   240
CGPLFVIDHA GSLTSQFSYV VGRSALRSTT GQARSADYGI TDCNPLPAND LTPEQKVAAA   300
ALLAPAAAAI VAGPKQNCEP DLMPYARPFA VGKRTCSGIV TP                      342

SEQ ID NO: 7                moltype = AA  length = 342
FEATURE                     Location/Qualifiers
REGION                      1..342
                            note = Synthetic
source                      1..342
                            mol_type = protein
                            organism = synthetic construct
SEQUENCE: 7
MKLLSLTGVA GVLATCVAAT PLVKRLPSGS DPAFSQPKSV LDAGLTCQGA SPSSVSKPIL    60
LVPGTGTTGP QSFDSNWIPL STQLGYTPCW ISPPPFMLND TQVNTEYMVN AITTLYAGSG   120
NNKLPVLTWS QGGLVAQWGL TFFPSIRSKV DRLMAFAPDY KGTVLAGPLD ALAVSAPSVW   180
QQTTGSALTT ALRNSGGLTQ IVPTTNLYSA TDEIVQPQVS NSPLDSSYLF NGKNVQAQAV   240
CGPLFVIDHA GSLTSQFSYV VGRSALRSTT GQARSADYGI TDCNPLPAND LTPEQKVAAA   300
ALLAPAAAAI VAGPKQNCEP DLMPYARPFA VGKRTCSGIV TP                      342

SEQ ID NO: 8                moltype = AA  length = 326
FEATURE                     Location/Qualifiers
REGION                      1..326
                            note = Synthetic
source                      1..326
                            mol_type = protein
                            organism = synthetic construct
SEQUENCE: 8
ALPSGSDPAF SQPKSVLDAG LTCQGASPSS VSKPILLVPG TGTTGPQSFD SNWIPLSTQL    60
GYTPCWISPP PFMLNDTQVN TEYMVNAITA LYAGSGNNKL PVLTWSQGGL VAQWGLTFFP   120
SIRSKVDRLM AFAPDYKGTV LAGPLDALAV SAPSVWQQTT GSALTTALRN AGGLTQIVPT   180
TNLYSATDEI VQPQVSNSPL DSSYLFNGKN VQAQAVCGPL FVIGHAGSLT SQFSYVVGRS   240
ALRSTTGQAR SADYGITDCN PLPANDLTPE QKVAAAALLA PAAAAIVAGP KQNCEPDLMP   300
YARPFAVGKR TCSGIVTPLE HHHHHH                                        326

SEQ ID NO: 9                moltype = AA  length = 342
FEATURE                     Location/Qualifiers
REGION                      1..342
                            note = Synthetic
source                      1..342
                            mol_type = protein
                            organism = synthetic construct
SEQUENCE: 9
MKLLSLTGVA GVLATCVAAT PLVKRLPSGS DPAFSQPKSV LDAGLTCQGA SPSSVSKPIL    60
LVPGTGTTGP QSFDSNWIPL SAQLGYTPCW ISPPPFMLND TQVNTEYMVN AITTLYAGSG   120
NNKLPVLTWS QGGLVAQWGL TFFPSIRSKV DRLMAFAPDY KGTVLAGPLD ALAVSAPSVW   180
QQTTGSALTT ALRNAGGLTQ IVPTTNLYSA TDEIVQPQVS NSPLDSSYLF NGKNVQAQAV   240
CGPLFVIDHA GSLTSQFSYV VGRSALRSTT GQARSADYGI TDCNPLPAND LTPEQKVAAA   300
ALLAPAAAAI VAGPKQNCEP DLMPYARPFA VGKRTCSGIV TP                      342

SEQ ID NO: 10               moltype = AA  length = 325
FEATURE                     Location/Qualifiers
REGION                      1..325
                            note = Synthetic
source                      1..325
                            mol_type = protein
                            organism = synthetic construct
SEQUENCE: 10
LPSGSDPAFS QPKSVLDAGL TCQGASPSSV SKPILLVPGT GTTGPQSFDS NWIPLSTQLG    60
YTPCWISPPP FMLNDTQVNT EYMVNAITAL YAGSGNNKLP VLTWSQGGLV AQWGLTFFPS   120
IRSKVDRLMA FAPDYKGTVL AGPLDALAVS APSVWQQTTG SALTTALRNA GGLTQIVPTT   180
NLYSATDEIV QPQVSNSPLD SSYLFNGKNV QAQAVCGPLF VIGHAGSLTS QFSYVVGRSA   240
LRSTTGQARS ADYGITDCNP LPANDLTPEQ KVAAAALMAP AAAAIVAGPK QNCEPDLMPY   300
ARPFAVGKRT CSGIVTPLEH HHHH                                          325

SEQ ID NO: 11               moltype = AA  length = 321
FEATURE                     Location/Qualifiers
REGION                      1..321
                            note = Synthetic
VARIANT                     313
                            note = misc_feature - Xaa can be any naturally occurring
```

-continued

```
                              amino acid
source                        1..321
                              mol_type = protein
                              organism = synthetic construct
SEQUENCE: 11
MALPSGSDPA FSQPKSVLDA GLTCQGASPS SVSKPILLVP GTGTTGPQSF DSNWIPLSTQ   60
LGYTPCWISP PPFMLNDTQV NTEYMVNAIT ALYAGSGNNK LPVLTWSQGG LVAQWGLTFF  120
PSIRSKVDRL MAFAPDYKGT VLAGPLDALA VSAPSVWQQT TGSALTTALR NAGGLTQIVP  180
TTNLYSATDE IVQPQVSNSP LDSSYLFNGK NVQAQAVCGP LFVIDHAGSL TSQFSYVVGR  240
SALRSTTGQA RSADYGITDC NPLPANDLTP EQKVAAAALL APAAAAIVAG PKQNCEPDLM  300
PYARPFAVGK RTXSGIVTPS L                                            321

SEQ ID NO: 12                 moltype = AA   length = 321
FEATURE                       Location/Qualifiers
REGION                        1..321
                              note = Synthetic
source                        1..321
                              mol_type = protein
                              organism = synthetic construct
SEQUENCE: 12
GAMALPSGSD PAFSQPKSVL DAGLTCQGAS PSSVSKPILL VPGTGTTGPQ SFDSNWIPLS   60
AQLGYTPCWI SPPPFMLNDT QVNTEYMVNA ITTLYAGSGN NKLPVLTASQ GGLVAQWGLT  120
FFPSIRSKVD RLMAFAPDYK GTVLAGPLDA LAVSAPSVWQ QTTGSALTTA LRNAGGLTQI  180
VPTTNLYSAT DEVVQPQVSN SPLDSSYLFN GKNVQAQAVC GPLFVIDHAG SLTSQFSYVV  240
GRSALRSTTG QARSADYGIT DCNPLPANDL TPEQKVAAAA LLAPAAAAIV AGPKQNCEPD  300
LMPYARPFAV GKRTCSGIVT P                                            321

SEQ ID NO: 13                 moltype = AA   length = 321
FEATURE                       Location/Qualifiers
REGION                        1..321
                              note = Synthetic
source                        1..321
                              mol_type = protein
                              organism = synthetic construct
SEQUENCE: 13
GAMALPSGSD PAFSQPKSVL DAGLTCQGAS PSSVSKPILL VPGTGTTGPQ SFDSNWIPLS   60
AQLGYTPCWI SPPPFMLNDT QVNTEYMVNA ITTLYAGSGN NKLPVLTWSQ GGLVAQWGLT  120
FFPSIRSKVD RLMAFAPDYK GTVLAGPLDA LAVSAPSVWQ LTTGSALTTA LRNAGGLTQI  180
VPTTNLYSAT DEAVQPQVSN SPLDSSYLFN GKNVQAQAVC GPLFVIDHAG SLTSQFSYVV  240
GRSALRSTTG QARSADYGIT DCNPLPANDL TPEQKVAAAA LLAPAAAAIV AGPKQNCEPD  300
LMPYARPFAV GKRTCSGIVT P                                            321

SEQ ID NO: 14                 moltype = AA   length = 321
FEATURE                       Location/Qualifiers
REGION                        1..321
                              note = Synthetic
source                        1..321
                              mol_type = protein
                              organism = synthetic construct
SEQUENCE: 14
GAMALPSGSD PAFSQPKSVL DAGLTCQGAS PSSVSKPILL VPGTGTTGPQ SFDSNWIPLS   60
AQLGYTPCWI SPPPFMLNDT QVNTEYMVNA ITTLYAGSGN NKLPVLTWSQ GGLVAQWGLT  120
FFPSIRSKVD RLMAFAPDYK GTVLAGPLDA LAVSAPSVWQ QTTGSALTTA LRNAGGLTQI  180
VPTTNLYSAT DEICQPQVSN SPLDSSYLFN GKNVQAQAVC GPLFVIDHAG SLTSQFSYVV  240
GRSALRSTTG QARSADYGIT DCNPLPANDL TPEQKVAAAA LLAPGVAAIV AGPKQNCEPD  300
LMPYARPFAV GKRTCSGIVT P                                            321

SEQ ID NO: 15                 moltype = AA   length = 342
FEATURE                       Location/Qualifiers
REGION                        1..342
                              note = Synthetic
source                        1..342
                              mol_type = protein
                              organism = synthetic construct
SEQUENCE: 15
MKLLSLTGVA GVLATCVAAT PLVKRLPSGS DPAFSQPKSV LDAGLTCQGT SPTSVTKPIL   60
LVPGTGTTGP GSFDSNWIPL STQLGYTPCW ISPPPFMLND TQVNTEYMVN AITTLYAGSG  120
NRKLPVLTWS QGGLVAQWGL TFFPSIRSKV DRLMAFAPDY KGTVLAGPLD ALAVSAPSVW  180
QQTTGSALTT ALRNAGGLTQ IVPTTNLYSA TDEIVQPQVS NSPLDSSYLF NGKNVQAQAV  240
CGPLFVIDHA GSLTSQFSYV VGRSALRSTT GQARSADYGI TDCNPLPAND LTPEQKVAAA  300
ALLAPAAAAI IAGPKQNCEP DLMPYARPFA VGKRTCSGIV TP                     342

SEQ ID NO: 16                 moltype = AA   length = 342
FEATURE                       Location/Qualifiers
REGION                        1..342
                              note = Synthetic
source                        1..342
                              mol_type = protein
                              organism = synthetic construct
```

```
SEQUENCE: 16
MKLLSVSGIV GVLATCVAAT PLVKRLPTGS DPAFSQPKSV LDAGLTCQGT SPTSVTKPIL   60
LVPGTGTTGP GSFDSNWIPL STQLGYTPCW ISPPPFMLND TQVNTEYMVN AITTLYAGSG   120
NRKLPVLTWS QGGLVAQWGL TFFPSIRSKV DRLMAFAPDY KGTVLAGPLD ALAVSAPSVW   180
QQTTGSALTT ALRNAGGLTQ IVPTTNLYSA TDEIVQPQVS NSPLDSSYLF NGKNVQAQAV   240
CGPLFVIDHA GSLTSQFSYV VGRSALRSTT GQARSADYGI TDCNPLPAND LTPEQKVAAA   300
ALLAPAAAAI IAGPKQNCEP DLMPYARPFA VGKRTCSGIV TP                      342

SEQ ID NO: 17          moltype = AA  length = 321
FEATURE                Location/Qualifiers
REGION                 1..321
                       note = Synthetic
source                 1..321
                       mol_type = protein
                       organism = synthetic construct
SEQUENCE: 17
GAMALPSGSD PAFSQPKSVL DAGLTCQGAS PSSVSKPILL VPGTGTTGPQ SFDSNWIPLS   60
AQLGYTPCWI SPPPFMLNDT QVNTEYMVNA ITTLYAGSGN NKLPVLTASQ GGLVAQWGLT   120
FFPSIRSKVD RLMAFAPLYK GTVLAGPLDA LAVSAPSVWQ QTTGSALTTA LRNAGGLTQI   180
VPTTNLYSAT DEMCQPQVSN SPLDSSYLFN GKNVQAQAVC GPLFVIDHAG SLTSQFSYVV   240
GRSALRSTTG QARSADYGIT DCNPLPANDL TPEQKVAAAA LLAPAAAAIV AGPKQNCEPD   300
LMPYARPFAV GKRTCSGIVT P                                             321

SEQ ID NO: 18          moltype = AA  length = 321
FEATURE                Location/Qualifiers
REGION                 1..321
                       note = Synthetic
source                 1..321
                       mol_type = protein
                       organism = synthetic construct
SEQUENCE: 18
GAMALPSGSD PAFSQPKSVL DAGLTCQGAS PSSVSKPILL VPGTGTTGPQ SFDSNWIPLS   60
AQLGYTPCWI SPPPFMLNDT QVNTEYMVNA ITTLYAGSGN NKLPVLTVSQ GGLVAQWGLT   120
FFPSIRSKVD RLMAFAPDYK GTVLAGPLDA LAGSAPSVWQ QTTGSALTTA LRNAGGLTQI   180
VPTTNLYSAT DEIVQPQVSN SPLDSSYLFN GKNVQAQAVC GPLFVIDHAG SLTSQFSYVV   240
GRSALRSTTG QARSADYGIT DCNPLPANDL TPEQKVAAAA LLAPYYAAIV AGPKQNCEPD   300
LMPYARPFAV GKRTCSGIVT P                                             321

SEQ ID NO: 19          moltype = AA  length = 321
FEATURE                Location/Qualifiers
REGION                 1..321
                       note = Synthetic
VARIANT                109
                       note = misc_feature - Xaa can be any naturally occurring
                        amino acid
source                 1..321
                       mol_type = protein
                       organism = synthetic construct
SEQUENCE: 19
GAMALPSGSD PAFSQPKSVL DAGLTCQGAS PSSVSKPILL VPGTGTTGPQ SFDSNWIPLS   60
AQLGYTPCWI SPPPFMLNDT QVNTEYMVNA ITTLYAGSGN NKLPVLTVXQ GGLVAQWGLT   120
FFPSIRSKVD RLMAFAPDYK GTVLAGPLDA LAGSAPSVWQ QTTGSALTTA LRNAGGLTQI   180
VPTTNLYSAT DEIVQPQVSN SPLDSSYLFN GKNVQAQAVC GPLFVIDHAG SLTSQFSYVV   240
GRSALRSTTG QARSADYGIT DCNPLPANDL TPEQKVAAAA LLAPYYAAIV AGPKQNCEPD   300
LMPYARPFAV GKRTCSGIVT P                                             321

SEQ ID NO: 20          moltype = AA  length = 321
FEATURE                Location/Qualifiers
REGION                 1..321
                       note = Synthetic
source                 1..321
                       mol_type = protein
                       organism = synthetic construct
SEQUENCE: 20
GAMALPSGSD PAFSQPKSVL DAGLTCQGAS PSSVSKPILL VPGTGTTGPQ SFDSNWIPLS   60
AQLGYTPCWI SPPPFMLNDT QVNTEYMVNA ITTLYAGSGN NKLPVLTVCQ GGLVAQWGLT   120
FFPSIRSKVD RLMAFAPDYK GTVLAGPLDA LAGSAPSVWQ QTTGSALTTA LRNAGGLTQI   180
VPTTNLYSAT DEIVQPQVSN SPLDSSYLFN GKNVQAQAVC GPLFVIDHAG SLTSQFSYVV   240
GRSALRSTTG QARSADYGIT DCNPLPANDL TPEQKVAAAA LLAPYYAAIV AGPKQNCEPD   300
LMPYARPFAV GKRTCSGIVT P                                             321

SEQ ID NO: 21          moltype = AA  length = 316
FEATURE                Location/Qualifiers
REGION                 1..316
                       note = Synthetic
source                 1..316
                       mol_type = protein
                       organism = synthetic construct
SEQUENCE: 21
```

```
AAIVAGPKQN CEPDLMPYAR PFAVGKRTCS GIVGLPSGSD PAFSQPKSVL DAGLTCQGAS    60
PSSVSKPILL VPGTGTTGPQ SFDSNWIPLS AQLGYTPCWI SPPPFMLNDT QVNTEYMVNA   120
ITTLYAGSGN NKLPVLTWSQ GGLVAQWGLT FFPSIRSKVD RLMAFAPDYK GTVLAGPLDA   180
LAVSAPSVWQ QTTGSALTTA LRNAGGLTQI VPTTNLYSAT DEIVQPQVSN SPLDSSYLFN   240
GKNVQAQAVC GPLFVIDHAG SLTSQFSYVV GRSALRSTTG QARSADYGIT DCNPLPANDL   300
TPEQKVAAAA LLAPAA                                                   316

SEQ ID NO: 22           moltype = AA  length = 331
FEATURE                 Location/Qualifiers
REGION                  1..331
                        note = Synthetic
source                  1..331
                        mol_type = protein
                        organism = synthetic construct
SEQUENCE: 22
LLAGAVVGTP LVKRLPGGSD PAFTQPQAVL DAGLTCQGAS PSSVSNPILL VPGTGTTGPG    60
SFDSNWIPLS TQLGYTPCWI SPPPFMLNDT QVNAEYMVNA VTKLYAGSGN KAVPVLTWSQ   120
GGLVAQWGLT FFPSIRGKVD RLMAFAPDYK GTVLAGILDA LSVAAPSVWQ QTAGSALTTA   180
LKNAGGLTQI VPTTNLYSAT DEVVQPQVSN SPLDSSYLFN AKNVQAQSVC GPLFVIDHAG   240
SLTSQFSYVV GRSALRSTSG QARSSDYSIT DCNPLPANDL TPEQKVAAAA LLVPAAAAIA   300
AGPKQNCEPD LMPYARRYAV GKITCSGIVT P                                  331

SEQ ID NO: 23           moltype = AA  length = 343
FEATURE                 Location/Qualifiers
REGION                  1..343
                        note = Synthetic
source                  1..343
                        mol_type = protein
                        organism = synthetic construct
SEQUENCE: 23
MKFSTLASLV AIAASAVTAT PLVERLPQGS DPAFSTPKSV LDAGLTCKNG SPSSQTKPIL    60
LVPGTGVTGE QNYDSNWIPL SSALGYSPCW VSPPPFMLND SQVNAEYIVN AVNVLYAGNG   120
NKKVPVLTWS QGGLATQWGL TFFPSIRSKV DRLMAFAPDY KGTIEASFLN AVGLSSQSIW   180
QQTSGSAYLT ALMNAGGLNQ IVPTTNLYSA TDEIVQPQIT NSPLDSSYLF NAKNIQAQTV   240
CGPLFIIDHA GSVTSQFSYV VGKSALGSPT GQAQSSDYGL TDCNPLPAND LTAEQKLESS   300
GLLLVAGANV IAGPKQNCEP DLKPYARRYA IGKRTCSGFV TPF                     343

SEQ ID NO: 24           moltype = AA  length = 475
FEATURE                 Location/Qualifiers
REGION                  1..475
                        note = Synthetic
source                  1..475
                        mol_type = protein
                        organism = synthetic construct
SEQUENCE: 24
MKVSLVKIAF TALMVSGISA HPTKELERRD LISNIDDIVN STIDNGEAHK DNAKSAITDI    60
FDKINDGIKQ DIDNLKEVGK SIADLIKSVV PTEDLSTPEG VQAYLGQLFE NGEDLFKNSI   120
DMVGHGLKPG SIAGNFEGFS DEINTSDNFN VKEPEGSVYP QAESEDPSFS LSEEQLRSAI   180
QIPEEFQYGN GSKSPVILVP GTGSKGGMTY ASNYAKLLKE TDFADVVWLN VPGYLLDDAQ   240
NNAEYVAYAI NYISGISNNK NVSIISWSQG GLDTQWALKY WASTRSKVSD FIPISPDFKG   300
TRMVPVLCPS FPKLSCPPSV LQQEYNSTFI ETLRADGGDS AYVPTTSIYS GFDEIVQPQS   360
GKGASGLIND NRNVGVTNNE VQTICPDRPA GKYYTHEGVL YNPVGYALAV DALTHEGPGQ   420
LSRIDLDTEC GRIVPDGLTY TDLLATEALI PEALVLILSY DDKTRDEPEI RSYAQ         475

SEQ ID NO: 25           moltype = AA  length = 463
FEATURE                 Location/Qualifiers
REGION                  1..463
                        note = Synthetic
source                  1..463
                        mol_type = protein
                        organism = synthetic construct
SEQUENCE: 25
MRWSSLLKAA VLYRAILSPL VSGAVIPRGA VPVASDLSLV SILSSAANDS SIESEARSIA    60
SLIASEIVSK IGKTEFSRST KDAKSVQEAF DKIQSIFADG TPDFLKMTRE ILTVGLIPAD   120
IVSFLNGYLN LDLNSIHNRN PSPKGQAIYP VKAPGDARYS VAENALRAAI HIPASFGYGK   180
NGKKPVILVP GTATPAGTTY YFNFGKLGSA ADADVVWLNI PQASLNDVQI NSEYVAYAIN   240
YISAISESNV AVLSWSQGGL DTQWALKYWP STRKVVDDFI AISPDFHGTV MRSLVCPWLA   300
ALACTPSLWQ QGWNTEFIRT LRGGGGDSAY VPTTTIYSTF DEIVQPMSGS QASAILSDSR   360
AVGVSNNHLQ TICGGKPAGG VYTHEGVLYN PLAWALAVDA LSHDGPGDPS RLDLDVVCGR   420
VLPPQLGLDD LLGTEGLLLI ALAEVLAYKP KTFGEPAIAS YAH                     463

SEQ ID NO: 26           moltype = AA  length = 420
FEATURE                 Location/Qualifiers
REGION                  1..420
                        note = Synthetic
source                  1..420
                        mol_type = protein
                        organism = synthetic construct
SEQUENCE: 26
```

-continued

```
MRFFTALSLF ISGAAIASAL PSSSETVEAN CVKPYLCCGE LKTPLDSTLD PILLDLGIDA  60
ASIVGSVGLL CLIPSKALTC LNGYAIIDLN SIHRHNPSPE NLSIYPYKAK SDAPYSIAEN  120
TLRAAIHIPR SFSHKRDKKI PVLLVPGTAV PAAITFYFNF GKLRRALPES ELVWIDLPQA  180
SLDDIQLSAE YVAYALNYVS ALTSSKIAVI SWSQGALDIQ WALKYWPSTR SVVNDFIAIS  240
PDFHGTIVKW LVCPLLNDLA CTPSIWQQGW DANFIQALRS QGGDSAYVTT TTIYSSFDKI  300
VRPMSGENAS ARLLDYRGVG VSNNHLQTIC ANNAAGGLYT HEGVLYNPLA WALTVDALLH  360
DGPSNITRID TQKICEQVLP PYLELTDMLG TEALLLVALA KILTYSPKVS GEPDIAKYAY  420

SEQ ID NO: 27          moltype = AA  length = 411
FEATURE                Location/Qualifiers
REGION                 1..411
                       note = Synthetic
source                 1..411
                       mol_type = protein
                       organism = synthetic construct
SEQUENCE: 27
MIFTSSPAVL LSTITLFAQL ALGLPTTSEP VHHESVRAIG ELSHRDELHD AGVVWNKVVR  60
QSPLVAPTDP RDSFNNQNPD VPGVGYPRSS DADPAFTIPE AKLRSAIYLP SGFNSSTNRQ  120
VVLFVPGTGA YGHESFADNL LKVITNAGAA DAVWVNVPNA MLDDVQSNAE YIAYAISYVK  180
ALIGDDRDLN VIGWSQGNLA TQWVLTYWPS TAPKVRQLIS VSPDFHGTML AYGLCAGNFG  240
KVAKAGAPCP PSVLQQLYSS NLINTLRAAG GGDAQVPTTS FWSRLTDEVV QPQAGLTASA  300
RMGDARNKGV TNVEVQTVCG LSVGGGQYGH STLMAHPLVA AMTLDALKNG GPASLSRIRS  360
QMFRACSNVV APGLQLTDRA KTEGLLATAG ARMGAFPTKL LREPALRQYA A            411
```